United States Patent
Bell et al.

(10) Patent No.: US 10,054,593 B2
(45) Date of Patent: Aug. 21, 2018

(54) MULTIPLEXED SPECTRAL LIFETIME DETECTION OF PHOSPHORS

(71) Applicants: INTELLIGENT MATERIAL SOLUTIONS, INC., Princeton, NJ (US); LEIDEN UNIVERSITY MEDICAL CENTER, Leiden (NL); THE UNITED STATES OF AMERICA, AS REPRESENTED BY THE SECRETARY, OF THE DEPARTMENT OF HEALTH AND HUMAN SERVICES, Washington, DC (US)

(72) Inventors: Howard Y. Bell, Princeton, NJ (US); Joshua E. Collins, Philadelphia, PA (US); Paul L. A. M. Corstjens, Leiderdorp (NL); Sukwan Handali, Norcross, GA (US); Hans J. Tanke, Rijnsburg (NL)

(73) Assignees: INTELLEIGENT MATERIAL SOLUTIONS, INC., Princeton, NJ (US); LEIDEN UNIVERSITY MEDICAL CENTER (NL); THE UNITED STATES OF AMERICA, AS REPRESENTED BY THE SECRETARY, OF THE DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 15/174,633

(22) Filed: Jun. 6, 2016

(65) Prior Publication Data
US 2016/0356780 A1     Dec. 8, 2016

Related U.S. Application Data

(60) Provisional application No. 62/171,320, filed on Jun. 5, 2015.

(51) Int. Cl.
*G01N 33/58* (2006.01)

(52) U.S. Cl.
CPC ....... *G01N 33/582* (2013.01); *G01N 2458/40* (2013.01)

(58) Field of Classification Search
None
See application file for complete search history.

(56) References Cited

U.S. PATENT DOCUMENTS

| | | |
|---|---|---|
| 5,043,265 A | 8/1991 | Tanke et al. |
| 7,858,396 B2 | 12/2010 | Corstjens et al. |
| 9,181,477 B2 | 11/2015 | Collins et al. |
| 2011/0306065 A1* | 12/2011 | Friedberg ............... B82Y 15/00 435/7.25 |
| 2016/0299076 A1 | 10/2016 | Katzlinger et al. |
| 2016/0299079 A1 | 10/2016 | Schramm et al. |

OTHER PUBLICATIONS

Corstjens et al., "Infrared up-converting phosphors for bioaasays," IEE Proc.—Nanobiotechnol., vol. 152, No. 2, Apr. 2005, pp. 64-72.
Corstjens et al., "Feasibility of a Lateral Flow Test for Neurocysticercosis Using Novel Up-Converting Nanomaterials and a Lightweight Strip Analyzer," PLOS Neglected Tropical Diseases, Jul. 2014, vol. 8, Issue 7, e2944, pp. 1-12.

* cited by examiner

*Primary Examiner* — Michelle F. Paguio Frising
(74) *Attorney, Agent, or Firm* — J.A. Lindeman & Co., PLLC

(57) ABSTRACT

New methods and assays for multiplexed detection of analytes using phosphors that are uniform in morphology, size, and composition based on their unique optical lifetime signatures are described herein. The described assays and methods can be used for imaging or detection of multiple unique chemical or biological markers simultaneously in a single assay readout.

8 Claims, 13 Drawing Sheets

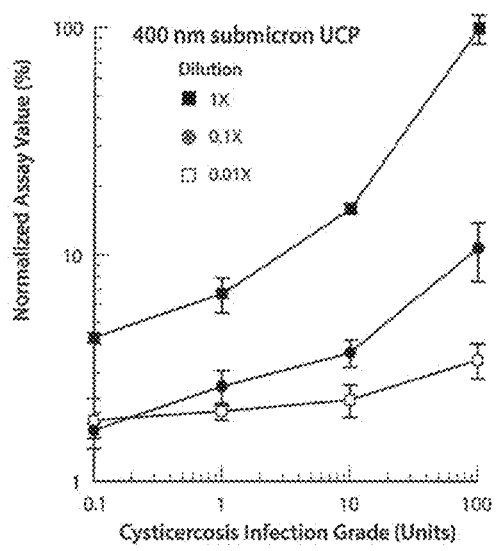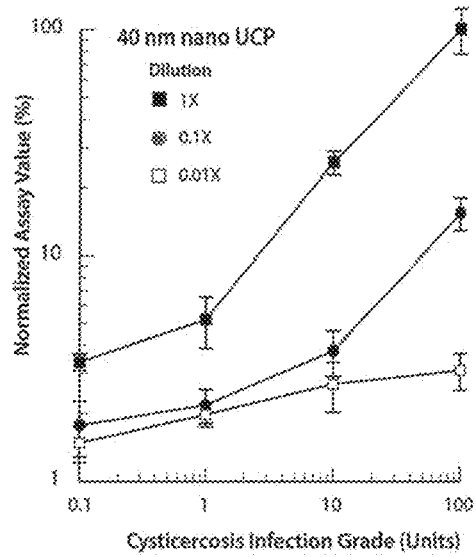
Fig. 10A
Fig. 10B

MULTIPLEXED SPECTRAL LIFETIME DETECTION OF PHOSPHORS

CROSS REFERENCE TO RELATED APPLICATIONS

This application claims priority to U.S. Patent Application 62/171,320, filed Jun. 5, 2015, the disclosure of which is incorporated herein by reference.

FIELD OF THE INVENTION

The invention relates to methods and assays for multiplexed detection and serialization of analytes using detectable phosphor labels where particular monodisperse phosphor particles are characterized by a uniform morphology, a uniform size, and/or composition and possesses their own unique optical spectral lifetime signatures.

BACKGROUND OF THE INVENTION

The invention relates generally to detectable labels and compositions useful in assay methods for detecting soluble, suspended, or particulate substances or analytes such as proteins, carbohydrates, nucleic acids, bacteria, viruses, and eukaryotic cells and more specifically relates to compositions and methods that include luminescent (e.g., phosphorescent) labels.

A detectable phosphor label is typically a phosphor conjugated with capture molecules that are specific for analytes of interest. Detectable phosphor labels can be used in all assay applications where fluorochrome, enzyme, or isotope-labelled immuno-reagents are used. Various phosphor conjugates, their preparation, and use were previously described in, for example, U.S. Pat. No. 5,043,265 (Tanke et al.), the disclosure of which is incorporated herein by reference. Examples of assay applications are enzyme-linked immunosorbent assay (ELISA), radioimmunoassay (RIA) techniques, and lateral flow assays for demonstrating and assaying an analyte in solution, immunological methods for the detection of macromolecules in filter blots, immunocytochemical methods for the study of morphologically intact tissues and cells, etc. As for the cytochemical applications, they usually target superficial antigens, as phosphor particles of 0.1-1.0 μm cannot easily penetrate cell membranes.

By using phosphors as detectable labels in an assay, several parameters can be studied and measured at the same time. Not only is it possible to generate three spectrally separate colours (blue, green, red) by means of infra red (IR), ultra violet (UV), or electron excitation, for example, but phosphor emission wavelengths and intensity aplitudes can be measured, and the number of analytes to be measured at the same time can become very large (multiplexing). Time-resolved luminescence assays are comparable in sensitivity to radioactivity assays. The immunocytochemical use of phosphor conjugates with capture molecules (analyte-specific phosphor conjugates) allows a much more sensitive detection of small quantities of macromolecules in cells. This may be of importance in both fundamental and diagnostic examination in various applications.

Examples of the properties of the phosphors, other than their high physico-chemical stability, are that they can be rendered visible by excitation with, for example, IR excitation, UV light, or with an electron beam, and that the luminescence of the phosphor-capture molecule conjugates, such as phosphor-antibody conjugates, does not decrease during excitation (no bleaching). In addition, the luminescence belongs to the relatively slow luminescence (phosphorescence). The luminescence of phosphors can be observed with microscope fluorimeters and flow cytometers. These can be modified for time-resolved luminescence assays in a relatively simple manner. The use of phosphor-capture molecule conjugates makes it possible to assay a plurality of analytes simultaneously, because the luminescence of phosphors is not only well separated spectrally (blue, green, red), but also exhibits measurable differences in decay times.

Prior multiplexing was generally performed by selective excitation and/or detecting the emission wavelength of the different phosphors. Simultaneous detection of multiple phosphors is possible, at least where the phosphors have the same excitation bands or different emission bands.

Currently there is a need for more rapid, ultrasensitive, and specific assays and methods that can image and detect multiple analytes in a sample in a single test assay readout. Because prior phosphor particles were not uniform in their morphology, size, and/or composition, it was not possible to detect analytes based on the unique optical lifetime signature of each type of phosphor in the conjugate being used as detectable label in an assay.

SUMMARY OF THE INVENTION

Disclosed herein, in certain embodiments, are methods for detecting one or more analytes in a sample (multiplexing), comprising the steps of: (a) contacting the sample with two or more types of phosphor particles, wherein each type of phosphor is conjugated to a capture molecule specific for an analyte of interest, to separately label each analyte of interest; (b) separating phosphor particles bound to the analytes from unbound phosphor particles; and (c) detecting each labelled analyte by the unique optical lifetime signature of the corresponding phosphor. The phosphor particles conjugated to each type of capture molecule have unique and uniform morphology, size, and/or composition, producing a unique optical lifetime signature.

Also disclosed are methods for detecting one or more analytes in a sample, wherein the detecting step is performed in a single readout. In another embodiment, the methods further comprise, before the step of contacting the sample with two or more types of phosphor particles, the step of capturing the one or more analytes on an analyte-specific capture molecule attached to a substrate.

Also disclosed herein are methods for detecting one or more analytes in a sample using two or more types of phosphor particles, wherein the phosphor particles are up-converting phosphor particles. These are up-converting phosphor particles comprise at least one rare earth element and a phosphor host material.

In some embodiments, the disclosed multiplexing methods for detecting one or more analytes in a sample are cell sorting methods, and the analytes of interest are cells. In other embodiments, the methods for detecting one or more analytes in a sample are used in flow cytometry.

In certain embodiments, the disclosed multiplexing methods can be performed using phosphor particles that are about 30 nm to about 400 nm in size.

Further disclosed are methods for multiplexed analyte detection in a sample, wherein the sample comprises a bodily fluid. In some embodiments, the bodily fluid sample can comprise blood serum, saliva, tissue fluid, or urine.

Also disclosed herein are assay kits for detecting one or more analytes in a sample. The disclosed kits include two or more types of phosphor particles conjugated to capture molecules specific for each analyte, and the phosphor particles conjugated to each type of capture molecule have unique and uniform morphology, size, and/or composition.

BRIEF DESCRIPTION OF THE FIGURES

FIG. 3 shows phosphor lifetime detection performed using 35 nm $NaYF_4$:YbEr nanocrystals sprayed onto a nitrocellulose membrane in a standard dilution series.

FIG. 7A shows the schematic of the UCP-rT24H lateral flow (LF) strip: Test line (T) 200 ng rT24H and Flow Control line (FC) 100 ng protein-A. FIG. 7B depicts the LF protocol for antibody detection (referred to as consecutive flow, CF) with the three sequential flow steps indicated.

FIG. 8A shows the test line (T-line) signal. FIG. 8B shows Ratio values. Both FIG. 8A and FIG. 8B indicate an optimum for the 2.5 U sample with the 200 ng rT24H Test. Assay results are presented as normalized assay values, percentage of the highest signal obtained with the 100 U infection reference.

FIG. 9 shows comparison of the UCP-rT24H assay with the ELISA (single blind evaluation with 141 clinical samples).

FIG. 10 shows the lower limit detection with sub-micron and nano-sized UCP partciles. FIG. 10A shows assay values for 400 nm submicron UCP. FIG. 10B depicts assay values for 40 nm nano UCP.

FIG. 11 shows the transmission of electron image of comparative phosphor particles.

DETAILED DESCRIPTION

Figure 1:
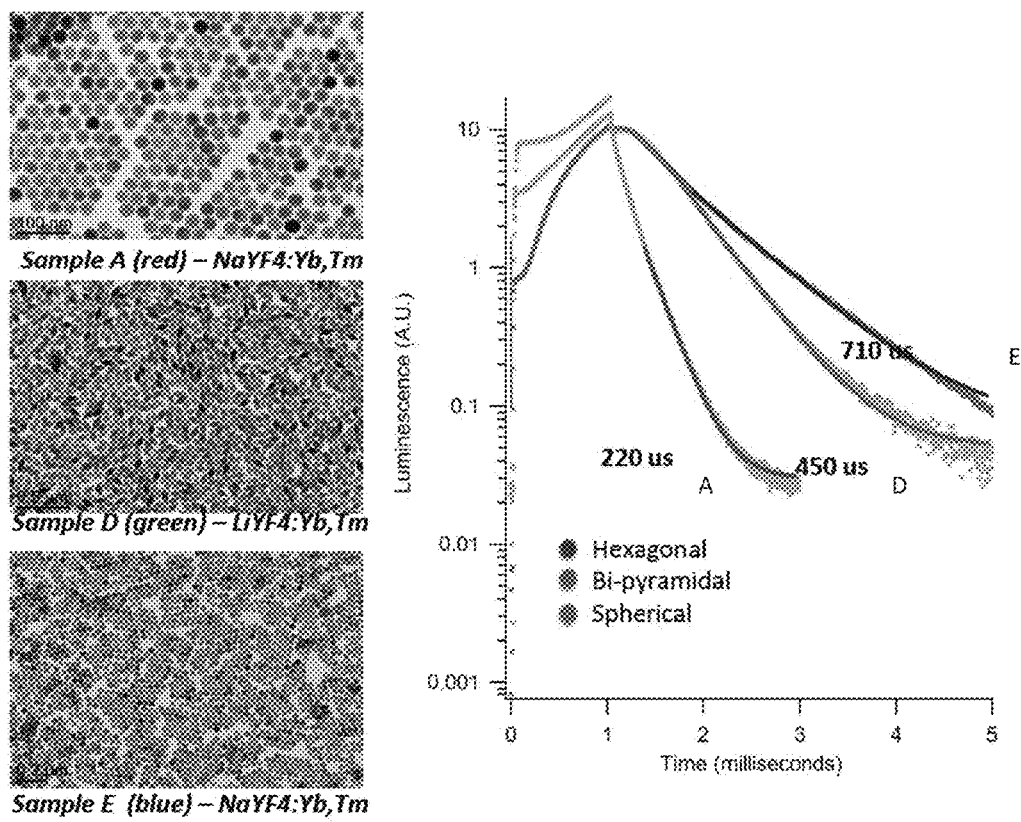
FIG. 1 shows Upconversion lifetime multiplexed detection of three unique particles (hexagonal Sample E blue, bi-pyramidal Sample D green, and spherical Sample A red) in a single suspension. Lifetimes can be tuned through particles' morphology, composition, and/or size.

The invention relates to new methods and assays for multiplexed detection of analytes using detectable phosphor labels where particular phosphor particles are characterized by a uniform morphology, a uniform size, and/or composition and possesses their own unique optical spectral lifetime signatures. The detectable phosphor labels are phosphor-capture molecule conjugates. Any capture molecule known in the art may be used and applied to the phosphor using means known in the art. See, for example, U.S. Pat. No. 5,043,265 (Tanke et al.) and U.S. Pat. No. 5,043,265 (Zarling, et al.), the disclosures of which are incorporated herein by reference. For each unique phosphor-capture molecule conjugate used as a detectable phosphor label in the invention, the particular phosphor is characterized by its own uniform morphology, a uniform size, and/or composition and possesses its own unique optical spectral lifetime signatures. The conjugate molecule is specific for a particular analyte of interest. This allows for multiple analytes to be detected by using multiple and different detectable phosphor labels. The presence or absence of a particular analyte is determined by whether or not the unique optical lifetime signature of the particular phosphor is observed.

The detectable phosphor labels of the invention may be used in any assay form where phosphor labels or particulate labels are used, such as those discussed above. Accordingly the methods and assays of the invention using the detectable phosphor labels can have a variety of applications, including chemical and biological detection and imaging. The described methods can be used for detection and/or imaging of multiple unique chemical or biological markers simultaneously in a single test assay and single readout. The assay may be a qualitative or a quantitative assay.

The detectable phosphor labels of the invention are prepared by conjugating a capture molecule, such as, but not limited to, an antibody or a protein specific for the analyte being screened for, to the phosphor particles as is known in the art. The phosphor particle may be coated with a surface modifier such as a poly (acrylic acid) polymer or an inert silica layer to allow or improve the cojugation of the capture molecule to the particle surface. The phosphor particles are rare earth nanocrystals or submicron phosphor monodisperse particles having uniform morphology and a uniform size. Such phosphor particles can then be detected in various assay formats and identified by their unique optical lifetime signature.

The use of phosphors as labels provides a rapid, multiplexed, and specific assay platform capable of detecting low levels of circulating analyte targets in human and non-human biological samples, such as, but not limited to, blood, saliva, tissue, and urine.

One such platform described herein, refers to a lateral flow assay format where the phosphor particle in the detectable label may be an up-converting phosphor (UCP) but where, instead of detecting the up-converting emission wavelength, the phosphor lifetime signature is detected. Up-conversion luminescence using rare-earth doped nanocrystals and submicron particles is increasingly being used in commercial and industrial applications and more recently has been used in life science applications. Up-conversion luminescence is based on the absorption of two or more low-energy (longer wavelength, typically infrared) photons by a nanocrystal followed by the emission of a single higher-energy (shorter wavelength) photon. Some aspects of lateral flow assays using UCP's—but not the use of phosphor labels where the phosphor lifetime signature is detected—have been described in Corstjens et al. (2014), Feasibility of Lateral Flow Test for Neurocysticercosis Using Novel Up-Converting Nanomaterials and a Lightweight Strip Analyzer, PloS Negl. Trop. Dis. 8(7):e2944. Doi:10.1371/journal.pntd.0002944, which is incorporated here by reference.

The ability to adjust the size, morphology, absorption, emission, rise time, decay time, power density, and other properties of phosphor particles such as up-converting nanocrystals (UCNC) or submicron phosphor particles enables the formation of materials with an infinite amount of distinctive signatures. The versatility of the rare earth UCNC platform significantly increases the ability to have a broad detection capability using a single reader system. Additionally, the ability to optically tune the rare earth nanoparticle or submicron particle unique spectral fingerprints provides limitless multiplexing capabilities. Phosphor particles such as up-converting crystals and nanocrystals with sizes ranging from 5 nm to 400 microns have been prepared, and the morphology of the crystals can be spherical, hexagonal, cubic, rod-shaped, or diamond-shaped. UCNC do not photobleach and allow high power density excitation over long term exposure with simultaneous signal integration. They can be stored indefinitely without a decrease in light emitting efficiency and thus they allow repeated irradiation and analysis.

Suitable rare earth crystalline phosphors are the morphologically and size uniform, monodiseprse phosphor particles described in U.S. Pat. No. 9,181,477, which is incorporated herein in its entirety. These phosphors include up-converting and down-converting phosphor compositions. Sunstone Nanocrystals® from Intelligent Material Solutions® Inc. (IMS), for example, are a proprietary series of rare earth-doped nanocrystals of small size, high quantum efficiency, and high photoluminescent intensity functionalized for use in industrial and life sciences applications. These nanocrystals possess unique and inherent atomic states that allow the conversion of various wavelengths of light energy up and down the electromagnetic spectrum. Sunstone Nanocrystals are synthesized using specific compositions of individual rare earths and other host elements. Up-conversion luminescence by Sunstone Nanocrystals occurs through a combination of a trivalent rare-earth sensitizer (e.g., Yb, Nd, Er, or Sm) as the element that initially absorbs the electromagnetic radiation and a second lanthanide activator (e.g., Er, Ho, Pr, Tm) ion in an optical passive crystal lattice that serves as the emitting elements. By varying the concentrations and ratios of rare earths, different emission spectra can be elicited from the same combination of elements. By varying the concentrations and ratios of rare earths, different emission spectra can be elicited from the same combination of elements.

Multiple nanoparticles and microparticles possessing unique lifetimes and/or morphologies can be combined and introduced into or onto an analyte providing a unique detectable label that can be used for analyte detection. The rare earth nanoparticles are ideally suited for the proposed application because of their relatively long phosphorescence lifetime decays attributed to the trivalent rare earth (or lanthanide) metals.

Phosphorescence is emission of luminescence which involves an internal conversion process called intersystem crossing for populating triplet states from the lowest excited singlet state and returning to ground state yielding slow emissions decay rates (microseconds to milliseconds) compared to the fluorescence of organic fluorophores which emit photons returning to the ground state from an excited singlet state with rapid lifetime decays in the nanosecond time scale. "Pulse" or "time-domain" lifetime measurements can be used as opposed to frequency-domain (or phase modulation).

Relatively inexpensive time-gating approaches can be used instead for measurements of either steady-state luminescence or intensity decays (lifetimes) on timescales, in the case of phosphorescence, which conform to the microsecond speeds of most current image detector arrays such as CMOS and CCD linear or area sensor arrays as well as photodiode arrays, all of which also offer the potential benefit of being used to spectrally discriminate multiple single exponential decays differing according to their emission wavelengths. In this application, this advantage is exploited to enable a "multiplexing" capability whereby a mixture of rare earth nanoparticles differing in emission wavelengths (under single 980 nm excitation), as well as differing in pre-determined values for their emission intensities and average lifetimes are used to develop a capacity for a very large number of anti-counterfeiting coding sequence combinations.

Typically, an excited state population decays exponentially after turning off the excitation pulse by first-order kinetics, following the decay law, $I(t)=I_0 \exp(-t/\tau)$ whereby for a single exponential decay I(t)=time dependent intensity, $I_0$=the intensity at time 0 (or amplitude), and $\tau$=the average time a nanoparticle remains in the excited state (or $<t>$) and is equal to the lifetime. (The lifetime, $\tau$ ισ the inverse of the total decay rate, $\tau=(T+k_{nr})^{-1}$, where at time t following excitation, T is the emissive rate and $k_{nr}$ is the non-radiative decay rate). In general, the inverse of the lifetime is the sum of the rates which depopulate the excited state. The luminescence lifetime can be simply determined from the slope of a plot of lnI(t) versus t (equal to $1/\tau$) can also be the time needed for the intensity to decrease to 1/e of its original value (time 0). Thus, for any given known emission wavelength, a number of parameters fitting the exponential decay law can be monitored for their use in developing anti-counterfeiting codes.

The lifetimes of the phosphor particles can be precisely tuned for each emitted wavelength of the particle determined by the particle morphology and composition. For instance, particles of identical compositions have been shown to exhibit unique lifetime responses to an excitation source as can be seen in FIG. 1. Samples A (spherical, 220 μs) and E (hexagonal, 710 μs) possess identical compositions of NaYF$_4$:Yb,Tm, but have different morphologies yielding a unique lifetime signature.

Figure 2:
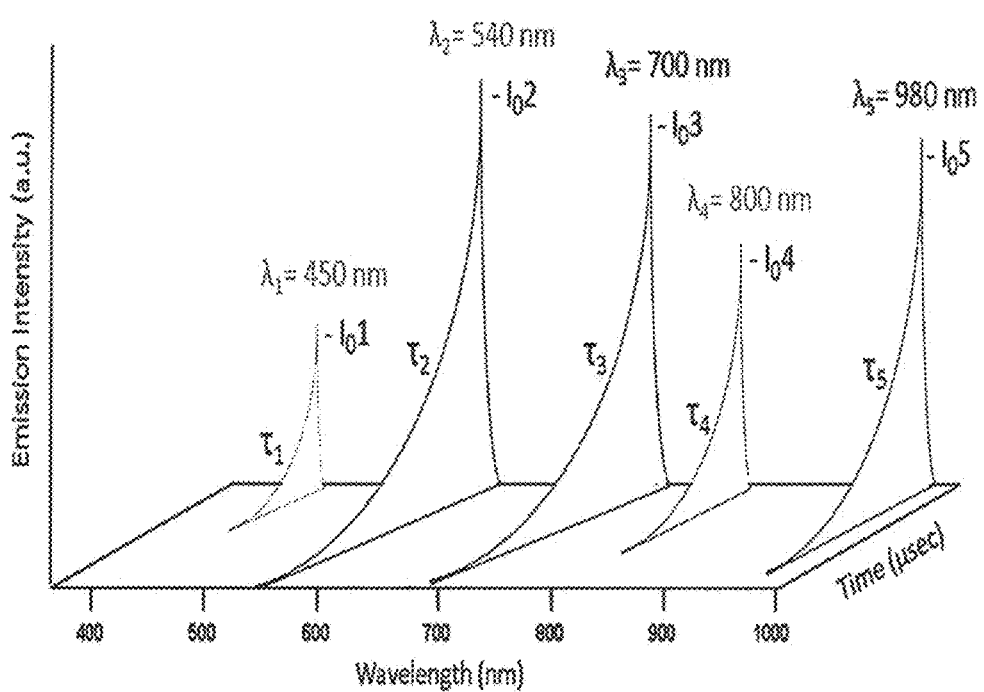
FIG. 2 depicts Upconversion multiplexed spectral lifetime detection of various rare earth nanoparticle compositions in a single readout.

As mentioned above, it is desirable to combine known emission wavelengths, intensity amplitudes, and lifetimes in this regard. FIG. 2 provides an example of the multiplexing capabilities of the nanoparticles. The figure depicts multiple nanoparticle emission signatures and lifetime decay profiles detected in a single sample or substrate for detectable labels of the invention which may be used in a multiplexed assay.

Disclosed herein, in certain embodiments, are methods for detecting one or more analytes in a sample (multiplexing). The disclosed methods include the steps of: (a) contacting the sample with two or more types of phosphor particles, wherein each type of phosphor is conjugated to a capture molecule specific for an analyte of interest, to separately bind and label each analyte of interest; (b) separating phosphor particles bound to the analytes from unbound phosphor particles; and (c) detecting each labelled analyte by the unique optical lifetime signature of the corresponding phosphor. In the disclosed multiplexing methods, the phosphor particles conjugated to each type of capture molecule have unique and uniform morphology, size, and/or composition, producing a unique optical lifetime signature.

Also disclosed are methods for detecting one or more analytes in a sample, wherein the detecting step is performed in a single readout. In some embodiments, the methods further comprise, before the step of contacting the sample with two or more types of phosphor particles, the step of capturing the one or more analytes on an analyte-specific capture molecule attached to a substrate.

Also disclosed herein are methods for detecting one or more analytes in a sample using two or more types of phosphor particles, where the phosphor particles are up-converting phosphor particles. These up-converting phosphor particles can comprise at least one rare earth element and a phosphor host material.

In some embodiments, the disclosed multiplexing methods for detecting one or more analytes in a sample are cell sorting methods, and the analytes of interest are cells. In certain other embodiments, the methods for detecting one or more analytes in a sample are used in flow cytometry.

In certain embodiments, the disclosed multiplexing methods can be performed using phosphor particles that are about 30 nm to about 400 nm in size.

Further disclosed are methods for multiplexed analyte detection in a sample, wherein the sample comprises a bodily fluid. In some embodiments, the bodily fluid sample can comprise blood serum, saliva, tissue fluid, or urine.

Also disclosed herein are assay kits for detecting one or more analytes in a sample. The disclosed kits include two or more types of phosphor particles conjugated to capture molecules specific for each analyte, and the phosphor particles conjugated to each type of capture molecule have unique and uniform morphology, size, and/or composition.

EXAMPLES

The following assays, methods, as well as ingredients, processes, and procedures for practicing the assays and methods disclosed herein correspond to that described above. The procedures below describe with particularity illustrative, non-limiting embodiments of the disclosed assays and methods.

Example 1

Figure 3A:
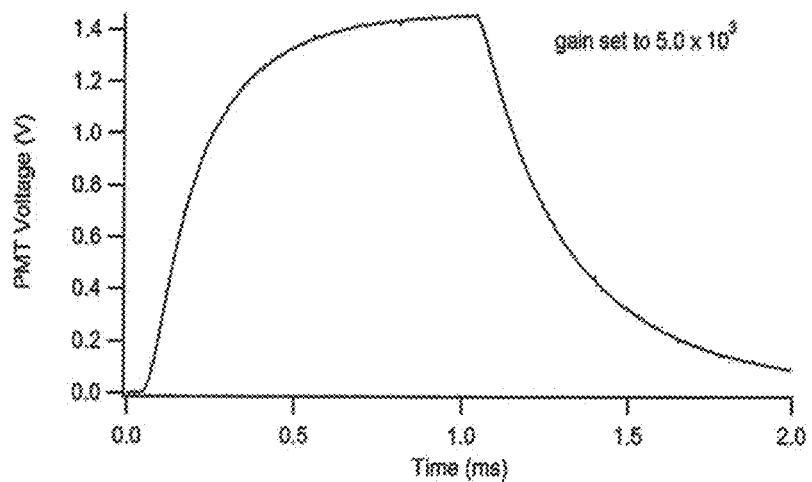
FIG. 3A shows time-dependent emission from 625 mg/μl concentration.
Figure 3B:
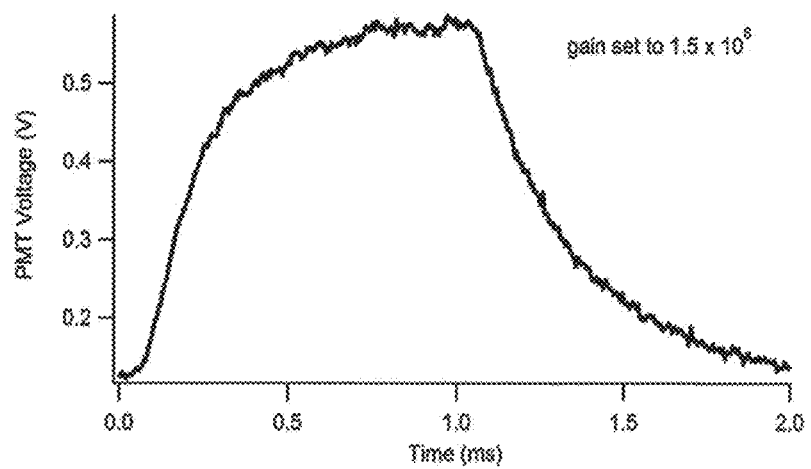
FIG. 3B depicts time-dependent emission from 40 mg/μl concentration.

Phosphor lifetime detection was performed using 35 nm $NaYF_4$:YbEr nanocrystals sprayed onto a nitrocellulose membrane in a standard dilution series. FIG. 3A shows time-dependent emission from 625 mg/µl concentration, and FIG. 3B depicts time-dependent emission from 40 mg/µl concentration.

The photomultiplier tube (PMT) gain was initially 0.4V control voltage (5×103), but was adjusted upward for the low range to 0.9V control voltage (1.5×106). The electronic gain was 105. No light-tight enclosure was used, so low level ambient light was present. The excitation source was a 2 W 980 nm laser, and the emission was filtered with a 700 nm short pass filter. The laser was turned on and off to allow for gated lifetime detection.

Figure 4:
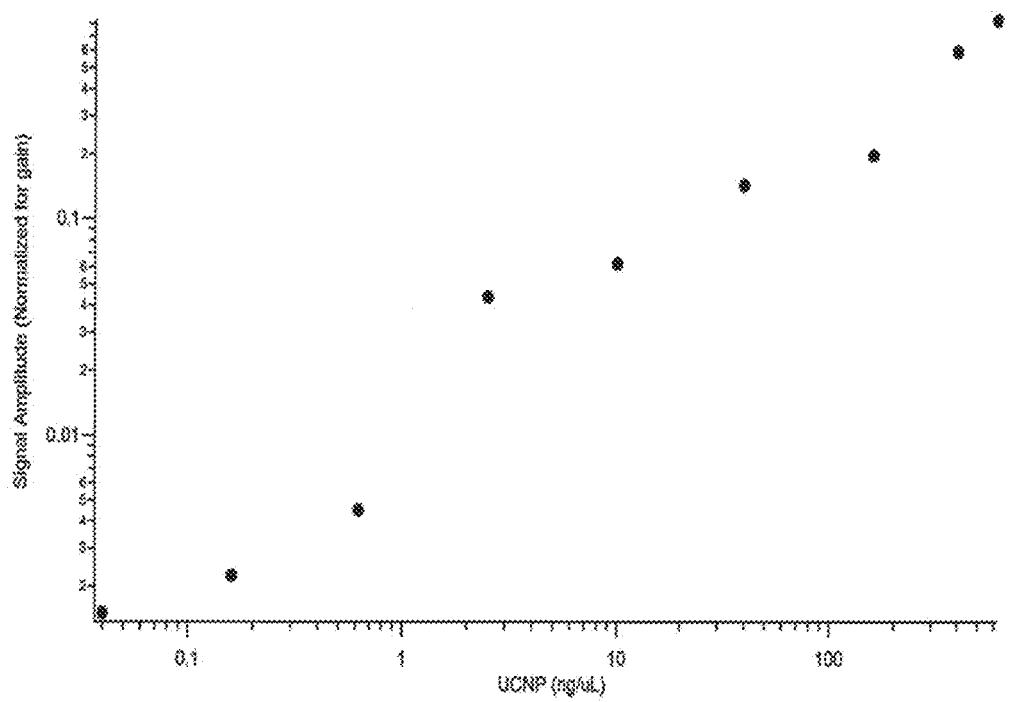
FIG. 4 depicts UCNP titration curve from Series A lateral flow assay (LFA) strips, after normalizing for additional gain on the low end (lowest 3 data points).

The time-dependent emission from the 625 ng/uL strip (FIG. 3A) was fit to a double-exponential, and the following parameters were found to best fit the data:

A1=0.53449±0.0921
tau1=0.15816±0.0108 ms
A2=0.80529±0.0838
tau2=0.39765±0.0334 ms The peak amplitude as a function of UCNP concentration, is shown in FIG. 4, which shows UCNP titration curve from Series A LFA strips, after normalizing for additional gain on the low end (lowest 3 data points).

To examine the sensitivity to transverse and z-axis focus, the signal from the 625 ng/uL spot was measured as a function of distance along the z-axis (FIG. 5) and transverse (FIG. 6) direction.

Figure 5:
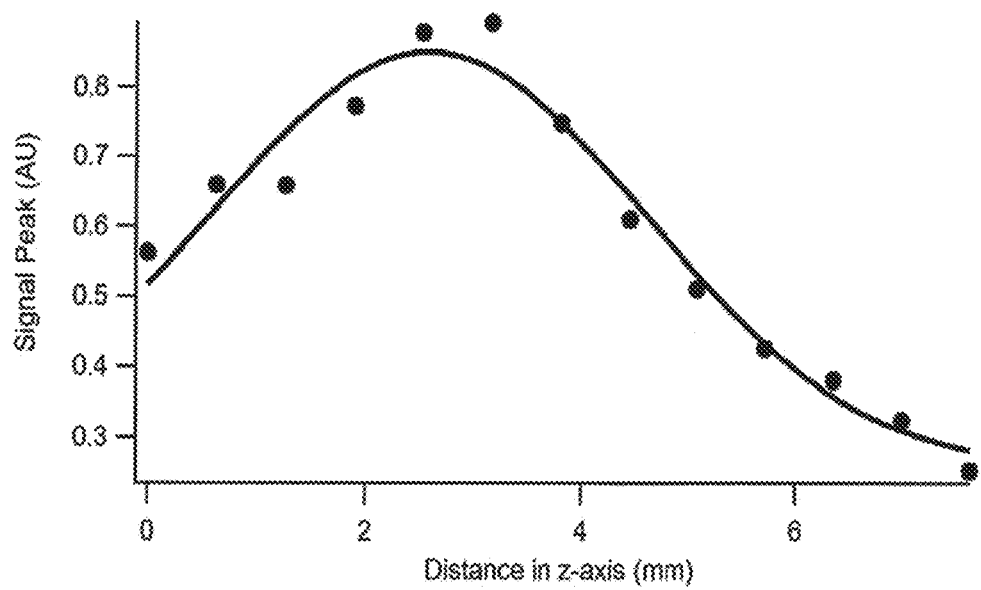
FIG. 5 shows the 625 ng/μL UCNP strip, where the focus in the z-axis was adjusted in increments of 0.025" and then converted to mm, and the resulting signal was plotted and fit to a Gaussian with a width of 2.8407±0.314 mm, showing relatively large insensitivity to z-axis.

FIG. 5 shows the 625 ng/uL UCNP strip. The focus in the z-axis was adjusted in increments of 0.025" and then converted to mm. The resulting signal was plotted and fit to a Gaussian with a width of 2.8407±0.314 mm, showing relatively large insensitivity to z-axis.

Figure 6:
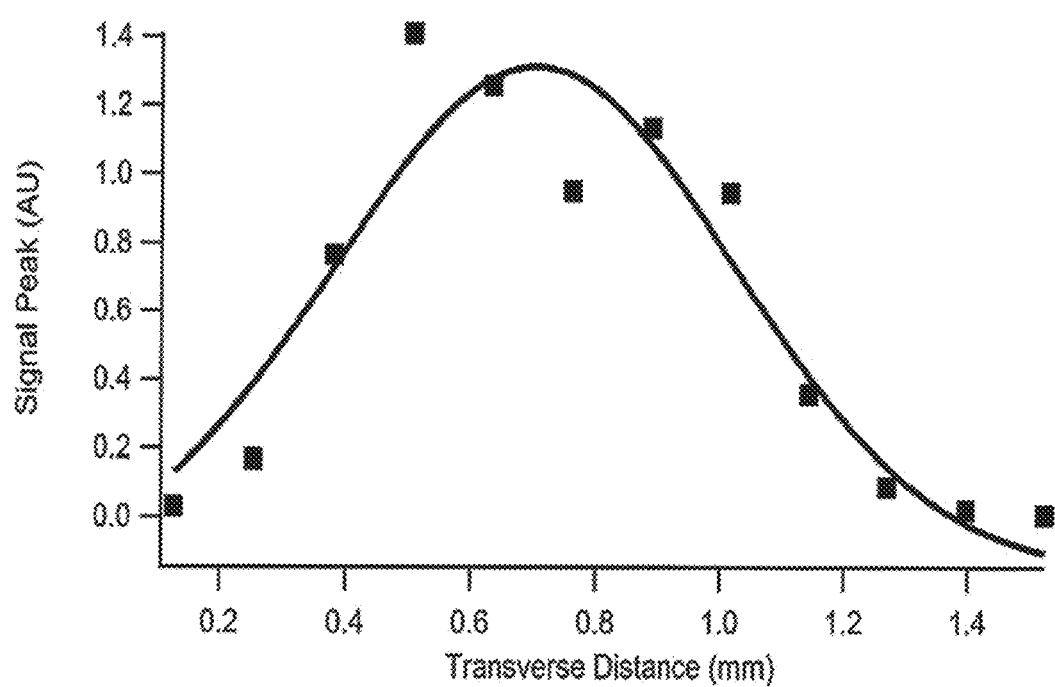
FIG. 6 depicts the results of measuring and plotting on the graph the signal in the transverse direction (presumably the direction of flow in a real assay) at optimal z-axis position in increments of 0.005". The signal was fit to a Gaussian, with width=0.45092±0.0934 mm.

The signal in the transverse direction (presumably the direction of flow in a real assay) was measured at optimal z-axis position in increments of 0.005" and plotted (FIG. 6). The signal was fit to a Gaussian, with width=0.45092±0.0934 mm.

Example 2

Figure 11A:
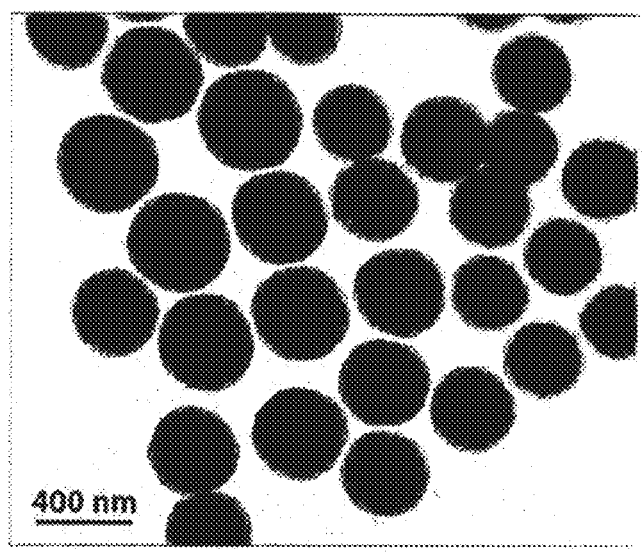
FIG. 11A shows transmission electron image of non-uniform-shape 400 nm $NaYF_4$:$Yb^{3+}$, $Er^{3+}$ up-converting phosphor particles (Corstjens et al., IEE Proc Nanobiotechnol 152: 64-72 (2005)).
Figure 11B:
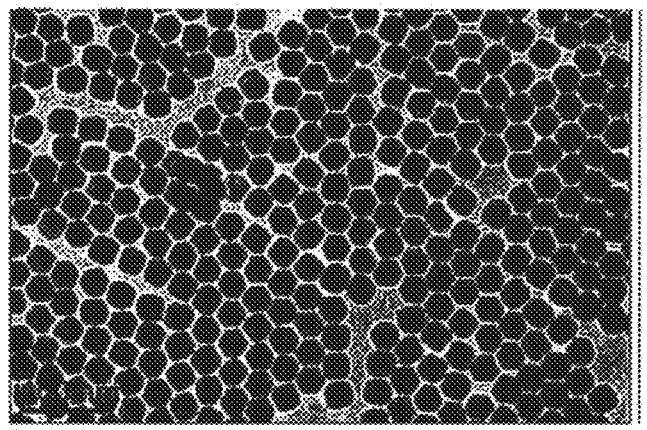
FIG. 11B shows transmission electron image of non-uniform-shape 400 nm $NaYF_4$:$Yb^{3+}$, $Er^{3+}$ up-converting phosphor particles (electron image of the uniform hexagonal 40 nm $NaYF_4$: $Yb^{3+}$, $Er^{3+}$ up-converting phosphor particles used as the detectable label for the proof-of-concept study in Example 2.
Figure 12:
FIG. 12 shows an image of the modified FluoroCount Packard benchtop reader for scanning multiple LF strips.
Figure 13:
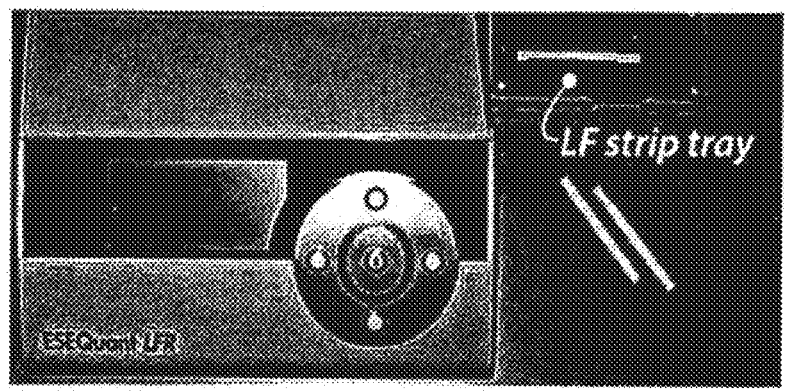
FIG. 13 shows an image of a portable, custom adapted, lightweight ESEQuant lateral flow strip reader LFR.

The following example has demonstrated proof-of-concept development with respect to usability and sensitivity of 40 nm sized $NaYF_4$:$Yb^{3+}$, $Er^{3+}$ polyacrylic acid-coated up-converting phosphor particles as UCNC reporter materials from Intelligent Material Solutions and analyzer equipment, where an up-conversion lateral flow assay format was used to detect neurcysticercosis. This proof-of-concept involved a single reporter material using a lateral flow assay format and detected the up-converted visible emission from the UCNC reporter materials. FIG. 11 shows the transmission of electron image of comparative phosphor particles. FIG. 11A shows transmission electron image of non-uniform-shape 400 nm $NaYF_4$:$Yb^{3+}$, $Er^{3+}$ up-converting phosphor particles (Corstjens et al., IEE Proc Nanobiotechnol 152: 64-72 (2005)). FIG. 11B shows transmission electron image of the uniform hexagonal 40 nm $NaYF_4$:$Yb^{3+}$, $Er^{3+}$ up-converting phosphor particles used as the detectable label for this proof-of-concept study. FIG. 12 shows an image of the modified FluoroCount Packard benchtop reader for scanning multiple LF strips. FIG. 13 shows the lateral flow strip reader and the $NaYF_4$:$Yb^{3+}$, $Er^{3+}$ up-converting phosphor particles.

Neurocysticercosis is a frequent parasitic infection of the human brain, occurring in most of the world, which requires imaging of the brain to diagnose. It is also the most frequent preventable cause of epilepsy in developing countries. To determine the burden of the disease and to simplify diagnosis, a low-cost, highly sensitive detection platform has been developed. The availability of a rapid serological diagnosis that targets stage-specific antibodies for human cysticercosis is considered very helpful in control programs for estimating the burden (sero-prevalence) of disease in susceptible population groups. A low-cost rapid diagnostic test could also be applied to determine sero-prevalence rates in pigs to assess interruption of transmission.

Figure 7:
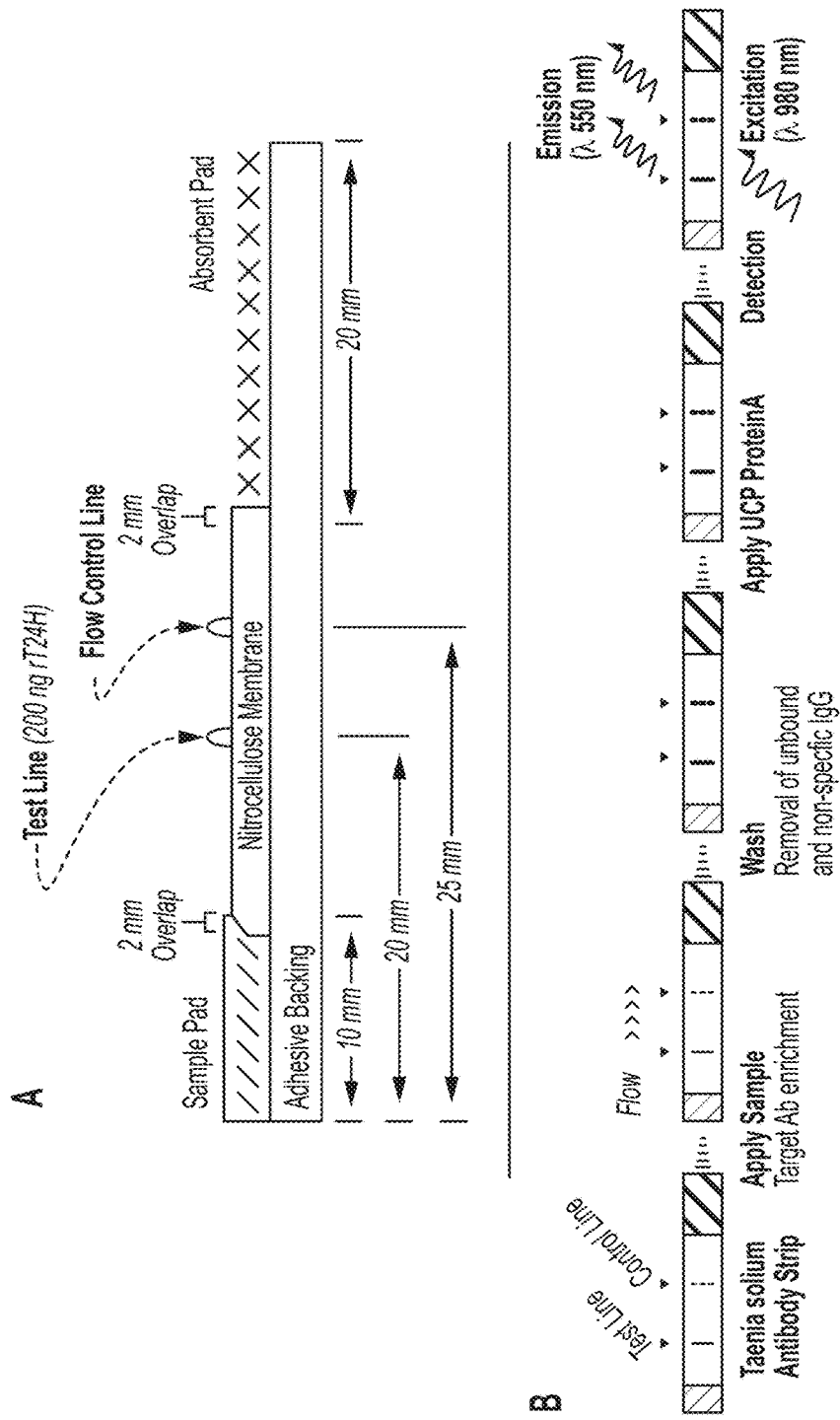
FIG. 7 shows a lateral flor test strip.

The up-converting phosphor lateral flow (UCP-LF) assay format used in this study was a consecutive flow assay (the sequential flow of sample, buffer, and UCP reporter particle), such as described in U.S. Pat. No. 7,858,396, which is incorporated herein by reference. It included the use of a generic UCP reporter (e.g., protein-A coated UCP particles) to detect human antibodies on a single lateral flow strip. The general protocol applied for the UCNC-LF assay used for the majority of the experiments in this study implied a dilution of sera in assay buffer such that 1 µL undiluted serum was delivered to the LF strips during the first flow step of the CF protocol (FIG. 7).

Serum Sample Load:

The performance of the UCNC-rT24H assay was first assessed with a set of sera with different reactivity ranging from 1 to 100 Units as determined by ELISA. The 2.5 Units sample is indicative for the targeted lower limit of detection (LLOD), a sample with low antibody titer. The general protocol applied for the UCNC-LF assay used for the majority of the experiments in this study, implied a dilution of sera in assay buffer such that 1 µL undiluted serum was delivered to the LF strips during the first flow step of the CF protocol (FIG. 7). The assay appeared to perform similar to previously described UCNC-CF antibody assays indicating high degree of flexibility towards sample input.

Figure 8:
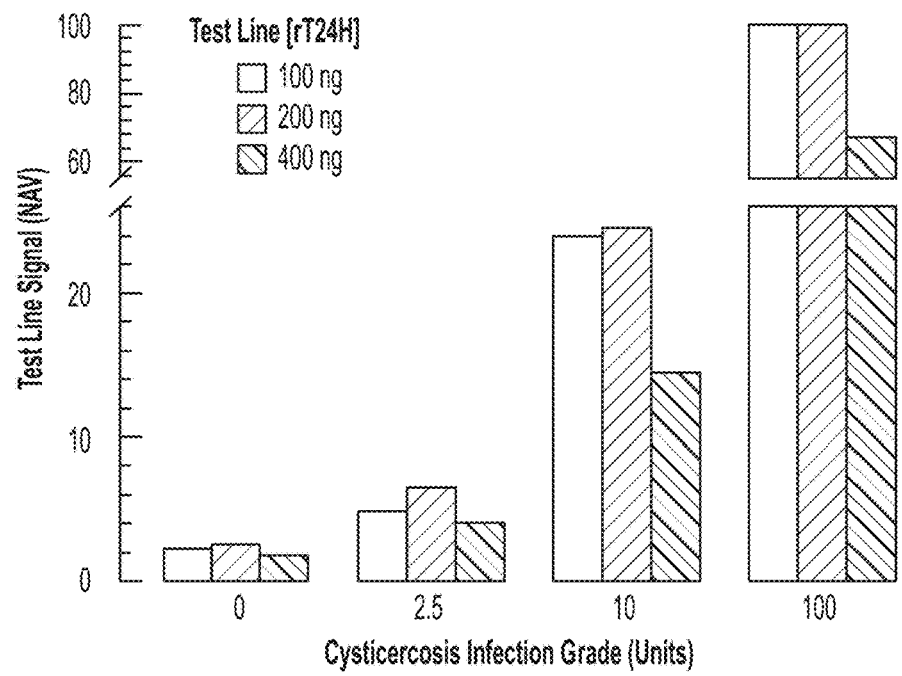
FIG. 8 depicts optimization of rT24H capture antigen load of the T-line. Performance of the up-conversion nanocrystals (UCNC)-rT24H assay with a standard reference panel of cysticercosis serum samples.
Figure 8:
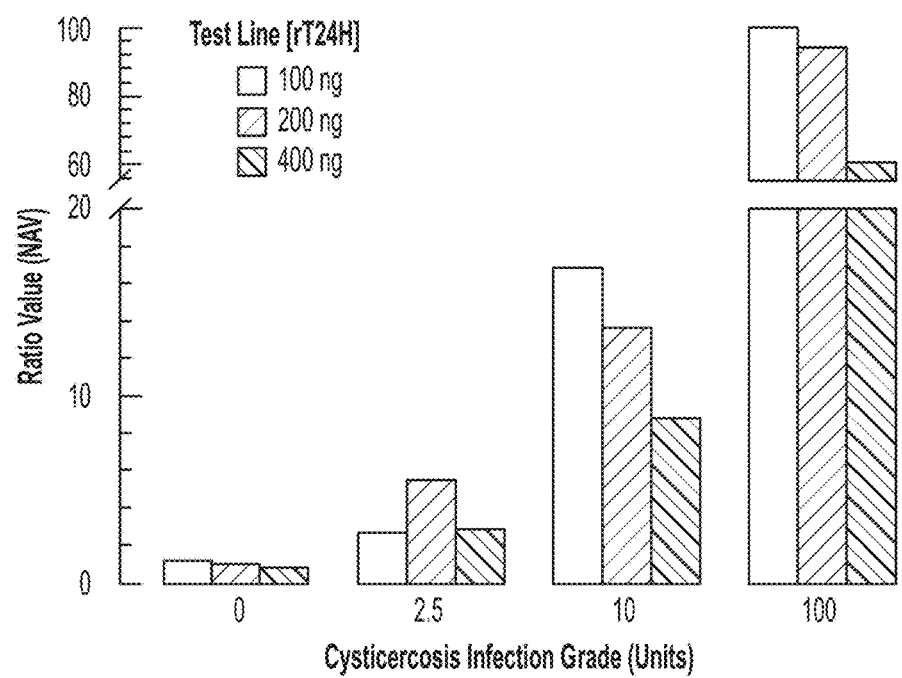

Amount of rT24H Antigen on the Test (T-)Line:

Often, the major production cost of LF-based assays is associated with the capture antigen on the T-line. The density (amount) of specific-antigen must be enough to prevent passing of the target molecules without interacting with the capture antigen. However, excess antigen on the T-line will lead to poor immobilization of the capture antigen on the LF strip, which can result in the unexpected loss of signal. For the UCNC-rT24H assay the T-line is comprised of purified rT24H. FIG. 8A shows the result of a typical experiment, indicating lower T-signal due to release when using 400 ng of rT24HNS antigen (per 4 mm width).

All assays were performed with the same amount of UCNC label, and T-signal values were normalized to the highest T-signal measured with the 100 Units sample; achieved with the LF strips containing an rT24H density of 100 ng, the 200 ng strips scored only a slightly lower signals. Differences become more pronounced when looking at normalized Ratio values (T-line signal divided by FC-line signal). An optimum around the targeted lower limit of detection (LLOD) of 2.5 Units with LF strips containing a T-line comprised of 200 ng rT24H seems apparent. A large difference between the zero and the sample indicative for the LLOD is essential to determine a solid assay cutoff threshold. The relative differences in Ratio values determined for the 0 and 2.5 Units samples were a factor of 2.16, 5.20 and 3.32 for the 100, 200 and 400 ng strips, respectively; corresponding A450 ELISA values (not shown) indicated a factor of 2.86. These values may differ when using differently sized UCNC particles; the experiment shown in FIG. 8 was performed with 400 nm particles, similar results were observed with the 40 nm particles. An additional constraint to consider is the sensitivity of the applied UCNC-LF strip scanner, which is the lowest UCNC signal that can be measured with the current UCNC reader.

Cutoff Threshold and Clinical Parameters:

The established UCNC-LF assay conditions used to validate the UCNC-rT24HNS neurocysticercosis antibody assay involved the use of 4 mm width LF strips with a T-line of 200 ng rT24H and the addition of the equivalent of 1 uL undiluted serum sample and 500 ng UCNC protein-A coated reporter particles. Testing of the clinical samples was performed in parallel with using both types of UCNC reporter particles: The 40 nm $NaYF_4$:Yb,Er particles with poly (acrylic acid) surface and the 400 nm sized $Y_2O_2S$:Yb,Tm particles with a silica coated carboxyl-functionalized surface.

Cutoff Threshold:

In order to assess clinical specificity, the assay cutoff threshold was evaluated with two sets of sera samples from healthy individuals following a protocol as described earlier (Corstjens et al., J. Clin. Microbiol. 2008) implying the definition of a low and high specificity cutoff threshold. The UCNC-rT24H ratio values were determined for both sample sets (92 Dutch blood donors and 78 healthy US residents) using both types of UCNC particles. Table 1 summarizes the determined values; the low specificity cutoff threshold was defined as the average Ratio value plus two times the standard deviation and the high specificity cutoff threshold was defined as the highest Ratio value in the control group plus two times the standard deviation.

TABLE 1

Cutoff threshold of the UCNC-rT24H assay.

| | 92 Dutch blood donors | | 78 USA residents | |
| --- | --- | --- | --- | --- |
| | 40 nm YF | 400 nm YOS | 40 nm YF | 400 nm YOS |
| Ratio: Average Value (AV) | 0.029 | 0.008 | 0.046 | 0.009 |
| Ratio: Highest Value (HV) | 0.110 | 0.026 | 0.186 | 0.033 |
| Standard Deviation: (SD) | 0.021 | 0.005 | 0.032 | 0.007 |
| Low specificity cutoff: AV + 2SD | 0.070 | 0.019 | 0.109 | 0.023 |
| High specificity cutoff: HV + 2SD | 0.151 | 0.037 | 0.231 | 0.047 |

Samples generating Ratio values below the low specificity cutoff were considered antibody negative with the UCNC-rTH24 test, samples above the high specificity cutoff were considered antibody positive. To determine the most likely classification of samples generating signals in between the low and high specificity cutoff, the determined threshold values need to be evaluated with a large, statistically relevant, set of confirmed positives. The significant difference in cutoff values when using YF or YOS UCNC particles is a technical issue that can be regulated by changing assay conditions (e.g., the amount of UCNC particles or the amount of rT24H on the Test line). The observed smaller difference in cutoff value between the two sets of healthy individuals tested with the same UCNC particles may indicate an effect based on cultural behavior and/or ethnicity.

Figure 9A:
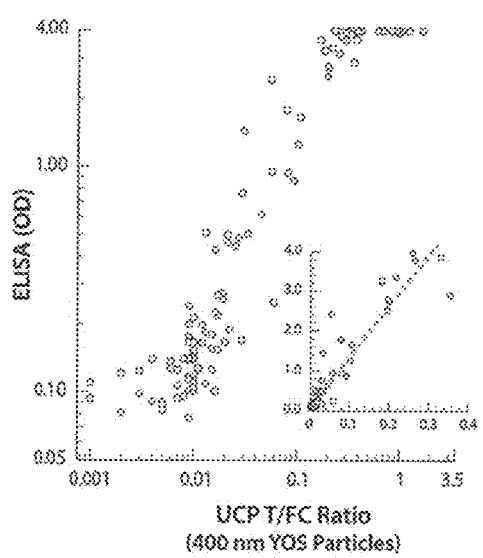
FIG. 9A shows comparison of Ratio values obtained with the 40 nm sized YF UCNC particles with the ELISA OD450 values.
Figure 9B:
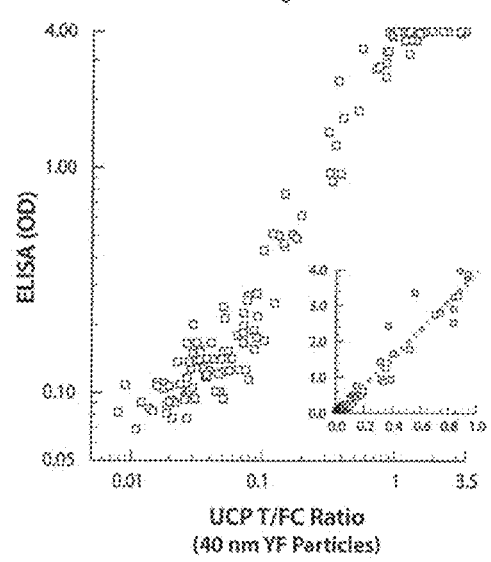
FIG. 9B depicts comparison of Ratio values obtained with the 400 nm sized YOS UCNC particles with the ELISA OD450 values.

Single Blinded Assay Validation:

Validation of the assay was accomplished with the selection banked serum samples of 63 classified cases of neurocysticercosis randomly arranged between the set of 78 serum samples from healthy US resident. The resulting 141 samples were tested with both types of UCNC particles in a single blind experiment. Obtained UCNC-rT24H Ratio values were plotted against the corresponding rT24H ELISA OD450 values (FIG. 9) showing a good correlation between the UCNC and ELISA.

Figure 9C:
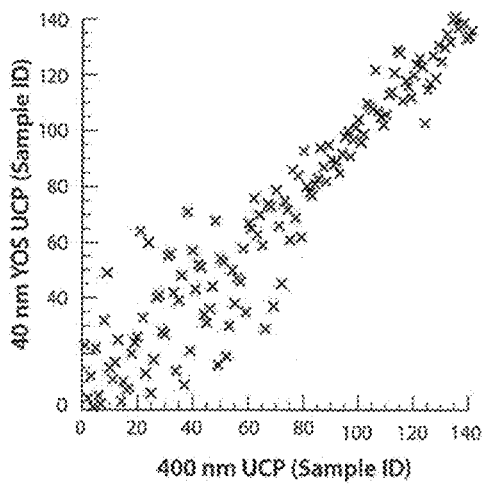
FIG. 9C shows Spearman ranking of the UCNC-rT24H Ratio values obtained with both types of UCNC particles, and the grey box indicates samples scoring values below the low specificity threshold (US resident control group).

The test conditions for the ELISA were set for best resolution in the low reactive range, implying a max OD450 value of 4 and thus no discrimination between high reactive samples. As observed when testing the cutoff threshold samples, the Ratio values determined with the 40 nm YF UCNC particles on average differed by a factor of ~4 compared to the Ratio values determined with the 400 nm YOS UCNC particles. Qualitatively both type of UCNC particles seem to perform quite similar, whereas quantitatively the 40 nm YF UCNC particles seem to correlate somewhat better with the ELISA. FIG. 9C, which is a scatter plot of the results obtained with the two types of UCNC particles, shows the Spearman correlation ($R^2$ is 0.90) of the Ratio values by rank order. The relatively large scattering of points in the lower range is directly linked to the low Ratio values measured for the non-reactive samples (indicated by the grey box).

Clinical Sensitivity and Specificity:

Application of the low and high specificity thresholds (Table 2) as determined with the 170 healthy controls indicated a number of UCNC-rT24H false positives and false negatives.

A sample was classified false positive (FP) when it is part of the set of healthy controls with a Ratio value score above the cutoff threshold, a sample was classified false negative (FN) when it is part of the set of defined cysticercosis set (with 2 or more cysts identified by microscopy). When using both low and high specificity thresholds, an indecisive (IND) or potentially positive group can be identified from samples scoring Ratio values between the low and high specificity threshold (Table 2).

applying the low specificity threshold determined for the Dutch blood bank donors, is 98% with a specificity of 88%. The actual required cutoff threshold is depending of the clinical sensitivity and specificity required demanded for this assay; in this respect the area of receiver operating characteristic (ROC) curves of the UCNC-rT24H indicate an area of 0.99 for both types of UCNC particles. In this particular test the low specificity threshold determined for the US resident group seems to deliver acceptable sensitivity/specificity levels of 96%/98% (Youden's index, J=0.933) and 94%/98% (J=0.919) for the 40 and 400 nm UCNC particles, respectively. For both particles, these numbers imply a positive and negative predictive value of 94% and 98%, respectively. With the ELISA 96% sensitivity is achieved with 94% specificity (J=0.898). These numbers indicate at least equivalent performance of the UCNC-rT24H assay as compared to the ELISA. Moreover, results show that in consecutive flow based assays [41] the 40 nm YF UCNC show significantly improved sensitivity over the 400 nm YOS UCNC particles.

Submicron-Versus Nano-Sized UCNC Particles:

The potential of a new type of UCNC particles, nano-sized 40 nm particles, was tested on LF strips containing T-lines with 200 ng rT24H antigen. In these experiments the 1 Unit standard sample was included rather than the 2.5 Units standard to allow exploration below the targeted LLOD, set a 2.5 Units. Four standard samples (0, 1, 10 and 100 Units) were diluted 10- and 100-fold in NHS and analyzed with UCNC-T24HNS assay using UCNC conjugates made with the 40 nm and 400 nm reporter particles. FIG. 10 shows the result of an experiment performed in triplicate, assay values were normalized to the highest Ratio value obtained with the 100 Units sample. Overall, the applied test conditions (500 ng UCNC conjugate per strip) seem to be in favor of the 40 nm nano-particles. This is demonstrated by the increase of the signal strength observed for 1 to 10 Units for the 40 nm particles: a factor of 7.69 versus 3.75 increase for the 40 and 400 nm particles,

TABLE 2

Performance of the UCNC-rT24H assay.

| UCNC Reporter | 40 nm YF UCNC particles | | | | 400 nm YOS UCNC particles | | | |
|---|---|---|---|---|---|---|---|---|
| Control group | Dutch donors | | US residents | | Dutch donors | | US residents | |
| Specificity threshold | Low | High | Low | High | Low | High | Low | High |
| Indecisive (IND) | 0 | 8 | 0 | 10 | 0 | 7 | 0 | 8 |
| False negative (FN), IND included | 1 | 1 | 3 | 1 | 2 | 4 | 4 | 0 |
| FN without IND | 1 | 9 | 3 | 11 | 2 | 11 | 4 | 8 |
| False positive (FP) in Dutch group | 6 | 0 | 1 | 0 | 5 | 0 | 2 | 0 |
| FP in US group | 18 | 1 | 3 | 0 | 7 | 0 | 2 | 0 |
| FP, Dutch + US group | 24 | 1 | 4 | 0 | 12 | 0 | 4 | 0 |
| Clinical Sensitivity (Sn)[a] | 98.4% | 87.5% | 95.5% | 85.1% | 96.9% | 85.1% | 94.0% | 88.7% |
| Clinical Specificity (Sp)[b] | 87.6% | 99.4% | 97.7% | 100.0% | 93.4% | 100.0% | 97.7% | 100.0% |
| Youden's index, J | 0.863 | 0.870 | 0.933 | 0.851 | 0.905 | 0.851 | 0.919 | 0.887 |

[a]Sn was calculated dividing the number of true positives (TP) by the sum of the number of TP + FN; TP are the 63 classified cysticercosis samples (Peru sample set)
[b]Sp was calculated dividing the number of true negatives (TN) by the sum of the number of TN + FN; TN are the 170 healthy control samples (Dutch and US sample set)

By definition, at 100% clinical specificity (Sp) all 170 healthy control samples should score a Ratio value below the cutoff threshold. For the assay with e.g. the 40 nm YF UCNC particles, this is achieved when using the high specificity threshold determined for the US resident group. Clinical sensitivity (Sn) of the assay then drops to 85%; for the 400 nm YOS UCNC particles at 100% specificity the sensitivity is 89%. The highest sensitivity, obtained when respectively. The 500 ng UCNC particles per LF strip matched well with the lightweight UCNC-Quant strip reader available for the analysis. IMS plans on further developing its nanocrystal synthesis and nanocrystal size and composition to increase the overall quantum efficiency (QE) of the UCNCs. Adjusting the nanocrystal composition as well as utilizing core shell structures, it is expected to see 10× increase in brightness.

The claimed invention is:

1. A method for detecting one or more analytes in a sample, comprising the steps of:
   (a) contacting the sample with two or more types of phosphor particles, wherein each type of phosphor is conjugated to a capture molecule specific for an analyte of interest, to separately bind and label each analyte of interest;
   (b) separating phosphor particles bound to the analytes from unbound phosphor particles; and
   (c) detecting each labelled analyte by the unique optical lifetime signature of the corresponding phosphor;
   wherein the phosphor particles conjugated to each type of capture molecule have unique optical lifetime signature and uniform morphology, size, and/or composition,
   wherein the phosphor particles are monodispersed, and
   wherein the phosphor particles are up-converting phosphor particles comprising at least one rare earth element and a phosphor host material.

2. The method of claim 1, wherein the detecting step is performed in a single readout.

3. The method of claim 1, further comprising, before step (a), the step of capturing the one or more analytes on an analyte-specific capture molecule attached to a substrate.

4. The method of claim 1, wherein the method is cell sorting method and the analyte of interest is a cell.

5. The method of claim 1, wherein the method is used in flow cytometry.

6. The method of claim 1, wherein the phosphor particles are about 30 nm to about 400 nm in size.

7. The method of claim 1, wherein the sample comprises a bodily fluid.

8. The method of claim 7, wherein the sample comprises blood serum, saliva, tissue fluid, or urine.

* * * * *